US005747320A

United States Patent [19]
Saha et al.

[11] Patent Number: 5,747,320
[45] Date of Patent: May 5, 1998

[54] **GLUCOSE AND CELLOBIOSE TOLERANT β-GLUCOSIDASE FROM *CANDIDA PELTATA***

[75] Inventors: Badal C. Saha, Peoria; Rodney J. Bothast, East Peoria, both of Ill.

[73] Assignee: The United States of America, as represented by the Secretary of Agriculture, Washington, D.C.

[21] Appl. No.: 691,757

[22] Filed: Aug. 2, 1996

[51] Int. Cl.$^6$ .............................. C12N 9/24; C12N 9/42; C12N 1/00

[52] U.S. Cl. .................. 435/209; 435/200; 435/161; 435/921

[58] Field of Search ................. 435/209, 200, 435/161, 921

[56] References Cited

PUBLICATIONS

Saha, Badal C., et al., "Thermostable β–Glucosidases", *Enzymatic Degradation of Insoluble Carbohydrates*, Chapter 13, reprinted from ACS Symposium Series No. 618, John N. Saddler & Michael H. Penner, 1995, pp. 197–207.

Saha, B.C., and Bothast, R. J., "Glucose Tolerant and Thermophilic β–Glucosidase from Yeasts", Program and Abstracts, 1995 SIM Annual Meeting, San Jose, CA, Aug. 6–11, 1995, Distributed Aug. 6, 1995.

Saha, Badal C., and Bothast, Rodney J., "Glucose Tolerant and Thermophilic β–Glucosidases from Yeasts,"*Biotechnology Letters*, vol. 18, No. 2, Feb. 1996, pp. 155–158.

Wright, John D., "Ethanol from Biomass by Enzymatic Hydrolysis", *Chemical Engineering Progress*, Aug. 1988, pp. 62–74.

Ladisch, M. R., et al., "Process considerations in the enzymatic hydrolysis of biomass", *Enzyme Microbiology Technology*, 1983, vol. 5, Mar., pp. 82–102.

Guenata et al. J. Sci. Food Agricult. vol. 50, 1990 pp. 499–506, Abstract enclosed.

Skory et al. Appl. Microbiol. Biotechnol. 1996 vol. 46, pp. 353–359.

Wright et al. Appl. Envir. Microbiol. vol. 58, 3455–3465, 1992.

*Primary Examiner*—Leon B. Lankford, Jr.
*Assistant Examiner*—Christopher R. Tate
*Attorney, Agent, or Firm*—M. Howard Silverstein; Randall E. Deck; John D. Fado

[57] ABSTRACT

A new β-glucosidase enzyme which is tolerant to glucose and cellobiose, and which is effective for the hydrolysis of cellobiose to glucose, is disclosed. The enzyme is produced by *Candida peltata*, strain NRRL Y-21603. This β-glucosidase may be used in conjunction with cellulolytic enzymes for the treatment of cellulosic materials to convert cellulose to glucose.

14 Claims, 5 Drawing Sheets

5,747,320

GLUCOSE AND CELLOBIOSE TOLERANT β-GLUCOSIDASE FROM *CANDIDA PELTATA*

BACKGROUND OF THE INVENTION

1. Field of the Invention

This invention relates to a β-glucosidase effective for hydrolyzing cellobiose to glucose, which has a high tolerance to glucose and cellobiose.

2. Background of the Invention

More than one billion gallons of ethanol are produced annually in the United States, with approximately 95% derived from fermentation of corn starch (Bothast, 1994, Genetically engineered microorganisms for the conversion of multiple substrates to ethanol, Proc. Corn Utilization Conf., National Corn Growers Assoc., St. Louis, Mo.). Various cellulosic agricultural residues such as corn stover, straw and bagasse can also serve as low-value and abundant feedstocks for production of fuel alcohol. Currently, the utilization of cellulosic biomass to produce fuel ethanol presents significant technical and economic challenges, and its success depends largely on the development of highly efficient and cost-effective biocatalysts for conversion of pretreated biomass to fermentable sugars.

Cellulolytic enzymes in conjunction with β-glucosidase act sequentially and synergistically to degrade cellulosic materials to glucose. This enzymatic saccharification involves the synergistic action of at least three different enzymes: (i) endo-1,4-β-glucanase (EC 3.2.1.4), (ii) exo-cellobiohydrolase (EC 3.2.1.91, an exo-1,4-β-glucanase) and (iii) 9-glucosidase (β-D-glucosidic glucohydrolase, EC 3.2.1.21). Endoglucanase and exo-cellobiohydrolase act synergistically upon cellulose to produce cellobiose which is then cleaved by β-glucosidase to glucose. Both endoglucanase and cellobiohydrolase activities are often inhibited by cellobiose (Coughlin, 1985, Biotechnol. Genet. Eng. Rev., 3:39–109; Kadam and Demain, 1989, Biochem. Biophys. Res. Commun., 161:706–711; and Woodward and Wiseman, 1982, Enzyme Microb. Technol., 4:73–79). 9-Glucosidase reduces cellobiose inhibition by hydrolyzing cellobiose to glucose, which allows the cellulolytic enzymes to function more efficiently (Saha et al., 1994, Appl. Environ. Microbiol., 60:3774–3780; and Xin et al., 1993, Enzyme Microb. Technol., 15:62–65). However, most microbial β-glucosidases that catalyze the hydrolysis of cellobiose are very sensitive to glucose inhibition, which limits their activity (Saha et al., 1995, Thermostable β-glucosidases. In: Enzymatic Degradation of Insoluble Carbohydrates. J. N. Saddler and M. H. Penner, Eds. pp. 197–207, American Chemical Society, Washington, D.C.; Gueguen et al., 1995, Enzyme Microb. Technol. 78: 900–906). Furthermore, the enzyme is also inhibited by its own substrate, cellobiose (Schmid and Wandrey, Biotechnol. Bioeng., 30:571–585; and Woodward and Wiseman, ibid). Glucose inhibition and thermal inactivation of β-glucosidase constitute two major barriers to the development of a commercial process for the enzymatic conversion of cellulosic biomass to glucose for the subsequent production of fuel ethanol (Woodward and Wiseman, ibid).

SUMMARY OF THE INVENTION

We have now discovered a new β-glucosidase enzyme which is tolerant to glucose and cellobiose, and is effective for the hydrolysis of cellobiose to glucose. The enzyme is produced by *Candida peltata*, strain NRRL Y-21603. This β-glucosidase may be used in conjunction with cellulolytic enzymes for the treatment of cellulosic materials to convert cellulose to glucose.

In accordance with this discovery, it is an object of this invention to provide a novel β-glucosidase enzyme for the enzymatic hydrolysis of cellobiose to glucose, which is glucose tolerant.

It is another object of this invention to provide a β-glucosidase enzyme which is effective for the hydrolysis of cellobiose even in the presence of high concentrations of glucose or cellobiose.

Still another object of this invention is to provide an improved process for the enzymatic conversion of cellulose to glucose and/or ethanol using a β-glucosidase insensitive to glucose and cellobiose inhibition.

Other objects and advantages of this invention will become readily apparent from the ensuing description.

DETAILED DESCRIPTION OF THE INVENTION

Figure 1:
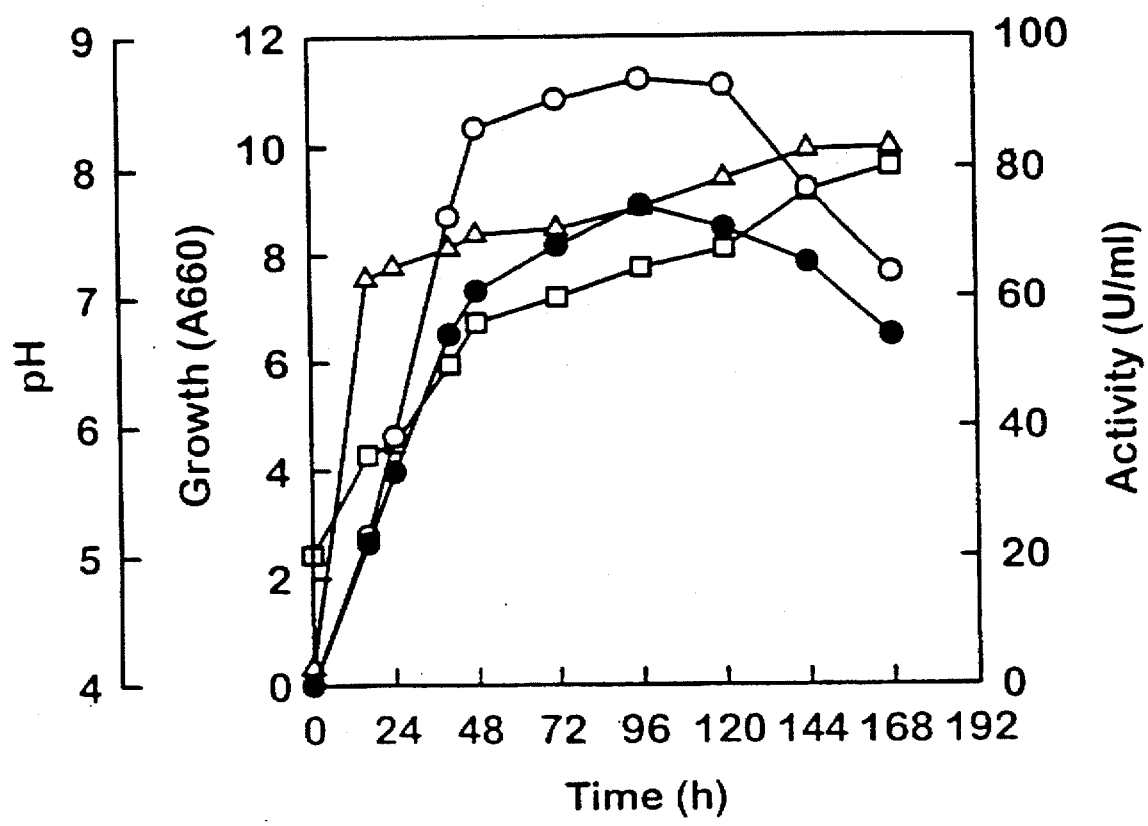
FIG. 1. Time course of β-glucosidase production by *Candida peltata* Y-21603 grown on glucose (1%, w/v) at 28° C. and 200 rpm. Symbols: □, pH; ▲, growth (A660), ○, β-glucosidase in whole culture broth; ●, β-glucosidase in culture supernatant.

The enzyme of this invention is a broad specificity β-D-glucosidase (EC 3.2.1.21) which is effective for the hydrolysis of cellobiose with the release of β-D-glucose therefrom. Surprisingly, the enzyme possesses an inhibition constant, $K_i$, with respect to glucose of about 1.4M, and crude preparations exhibit substantially no inhibition of activity at glucose concentrations less than or equal to about 12% (w/v). The enzyme retains its activity against cellobiose, almost completely hydrolyzing the compound to glucose, both in the presence and absence of glucose. Moreover, the enzyme is also highly tolerant to the substrate, cellobiose, and no inhibition has been observed at concentrations as high as 15% cellobiose.

The preferred microorganism for the production of the β-glucosidase of this invention is a strain of *Candida peltata*, strain NRRL Y-21603. The strain was deposited under the Budapest Treaty in the Agricultural Research Service Culture Collection in Peoria, Ill., on Jul. 26, 1996. This same strain of *Candida peltata* is also available from the general collection of the Agricultural Research Service Culture Collection under accession number NRRL Y-6888.

*Candida peltata* strain NRRL Y-21603 used in this invention was previously identified as *Torulopsis peltata*, strain CBS 5576. As described by Yarrow (1968, Antonie van Leeuwenhoek J. Microbiol. and Serology, 34:81–84), and Meyer et al. [1984, The Genus Candida, In: Kreger-van Rij (ed.), The Yeasts, a Taxonomic Study, Elsevier Press, Amsterdam, pp. 768–769], the contents of each of which are incorporated by reference herein, colonies grown on glucose-yeast extract-peptone agar at 25° C. for one month are greyish-white, either dull with reticulate markings or glistening and mucoid.

Morphologically, the cells grown in glucose-yeast extract-peptone water for 3 days at 25° C. are spherical to ovate, or lunate, (2.2–3.5)×(2.5–4.8)μm, occurring singly or in pairs. Neither mycelia nor pseudohyphae are formed. The strain will grow at 37° C. Glucose and galactose are fermented, while fermentation of sucrose and maltose may be negative or slow. A variety of carbon sources are assimilated, including cellobiose, glucose, galactose, L-sorbose, sucrose, maltose, trehalose, melezitose, soluble starch, D-xylose, D- or L-arabinose, D-ribose, L-rhamnose, D-glucosamine, glycerol, erythritol, ribitol, galactitol, adonitol, dulcitol, D-mannitol, D-sorbitol, D-glucitol, α-methyl-D-glucoside, salicin, lactic acid, succinic acid, and citric acid. Thiamine is essential for growth, and biotin and pyridoxine are stimulatory.

For the purposes of this invention, any isolate of *Candida peltata* having the identifying characteristics of strain NRRL Y-21603, including subcultures and variants thereof which retain the ability to produce glucose tolerant β-glucosidase, are effective for use herein. The term variant is defined herein to include transformants and mutants of *Candida peltata* which are capable of producing the enzyme.

Production of the β-glucosidase may be accomplished by culture of the aforementioned *C. peltata* isolates, using conventional techniques under aerobic conditions that are effective to promote growth and β-glucosidase production. Any number of well-known liquid or solid culture media may be used, although growth on liquid media is preferred as the enzyme is secreted into the media and recovery is simplified. Without being limited thereto, preferred liquid culture media include glucose-yeast extract-peptone water, Mycological broth, Sabouraud dextrose broth, Brain heart infusion broth, and Potato dextrose broth. Similarly, the media may contain a variety of carbon sources which will support growth and production of the enzyme, including those described above or in Example 1. However, optimal enzyme production has been obtained using glucose at low concentrations (i.e., about 4%), arabinose, and xylose. The yeast will grow and produce the β-glucosidase over wide pH and temperature ranges, with a pH of about 5.0 and a temperature between about 25°–30° C. being preferred.

Under these cultivation conditions, optimal production of β-glucosidase is achieved between about 48 to 120 hours, after which time enzyme production decreases gradually. Upon completion of the fermentation, preferably after about 4 to 5 days, the β-glucosidase may be isolated or separated from the yeast cells using techniques conventional in the art, such as by centrifugation or filtration.

As a practical matter, it is envisioned that commercial formulations of the β-glucosidase may be prepared directly from liquid culture medium from which cells have been removed in the above-described manner, thereby obviating the need to further purify the enzyme. However, in an alternative embodiment, the β-glucosidase remaining in the culture medium may be further concentrated and purified, particularly for applications demanding a high degree of purity where contamination by other enzymes, microbial products, or culture media components may be undesirable. Concentration and/or purification of the β-glucosidase may be effected by use of conventional techniques, including, but not limited to, ultrafiltration, dialysis, ion-exchange chromatography, HPLC, size-exclusion chromatography, cellobiose-sepharose affinity chromatography, and electrophoresis, such as polyacrylamide-gel-electrophoresis (PAGE). Using these techniques, β-glucosidase may be recovered in pure or substantially pure form. It is also envisioned that the enzyme may be formulated in conjunction with a suitable inert carrier or vehicle as known in the art. The skilled practitioner will recognize that such carriers must be compatible with the enzyme. Without being limited thereto, details of the preferred fermentation and separation procedures are described in the Examples.

When used in conjunction with a β-1→4 glucanase, the β-glucosidase is effective for hydrolyzing a variety of cellulosic materials to glucose. In accordance with this invention, cellulosic materials are defined herein as any cellulose containing material, and include but are not limited to crystalline or amorphous cellulose, and particularly lignocellulosic biomass such as agricultural residues (straws, hulls, stems, stalks), wood, municipal solid wastes (paper, cardboard, yard trash, and wood products), wastes from the pulp and paper industry, and herbaceous crops.

The β-1→4 glucanases used herein are recognized components of the cellulase complex, and include endo-1,4-glucanase (cellulase, E.C. 3.2.1.4) and exo-1,4-glucanase (exocellobiohydrolase, E.C. 3.2.1.91). In general, the process is based upon the well recognized synergistic action between β-glucosidase, endo-1,4-glucanase and exo-1,4-glucanase. When the cellulosic material is contacted with these glucanases, glucose and cellobiose are produced. The cellobiose thus formed is then converted to glucose by action of the β-glucosidase.

The particular source of the β-1→4 glucanases is not critical, and suitable enzymes may be obtained individually or in combination from commercial cellulase preparations, or they may be produced by culture of well known microorganisms, most notably *Trichoderma* species. Optimal hydrolysis of the cellulosic materials to glucose is achieved when the β-glucosidase is used in combination with both endo-1,4-glucanase and exo-1,4-glucanase. While both endo- and exo-1,4-glucanase hydrolyze cellulose to cellobiose and it is envisioned that the process could be practiced with only one of these enzymes, glucose yields would be significantly reduced. In addition, the presence of extraneous β-glucosidases, which may be contained in many commercial cellulase preparations, is not deleterious.

Hydrolysis of the cellulosic materials may be accomplished using conventional techniques. A number of processes have been previously described for the enzymatic hydrolysis of cellulosic or lignocellulosic materials, and are suitable for use with the enzymes described herein. These include, but are not limited to, those techniques reviewed by Wright (1988, Chem. Engin. Progress, 84(8):62–74) and Ladisch et al. (1983, Enzyme Microb. Technol., 5:82–102), the contents of each of which are incorporated by reference herein.

In general, the cellulosic material is contacted with catalytically effective amounts of the β-1→4 glucanases and β-glucosidase in an aqueous solution and under conditions effective to first hydrolyze cellulose to cellobiose, and then hydrolyze the cellobiose to glucose. The actual amount of enzyme and the conditions for the reaction will vary with the cellulosic substrate and the source of the β-1→4 glucanases, and may be readily determined. Optimal pH and temperature conditions for the β-glucosidase enzyme, are about 5.0° and 50° C., respectively. However, optimal conditions for the glucanases may be different. Typically, the pH will be between about 3.5 to 6.5, preferably between about 4.0 to 6.0, and the temperature will be between about 30° to 65° C., preferably between about 40° to 60° C. Owing to the glucose tolerance of the novel β-glucosidase, the concentrations of the enzymes may be lower than processes which have been previously described. Therefore, in the preferred embodiment, the enzymes are added in a concentration greater than or equal to about 5 IU/g cellulose.

The process may be conducted in conventional batch, fed-batch, or continuous reactor systems, such as described by Wang et al. (1979, Fermentation and Enzyme Technology, John Wiley & Sons, New York, pp. 339–343). Because the cellulosic substrate is insoluble, it is understood that the reaction should be conducted with agitation. Furthermore, the enzymes may be in solution or, in the alternative, immobilized onto a solid support. A number of techniques for the immobilization of β-1→4 glucanases and other β-glucosidases have been previously reported and may be used with the enzyme of this invention as well. Examples of suitable immobilization techniques and supports include, but are not limited to, those described by Woodward and Capps (1992, Appl. Biochem. Biotechnol., 34/35:341–347), Karube et al. (1977, Biotech. Bioeng., 19:1183–1191), Woodward and Zachry (1982, Enzyme Microb. Technol., 4:245–248), Srinivasan and Bumm (1974, Biotech. Bioeng., 16:1413–1418), Bissett and Sternberg (1978, Appl. Environ. Microbiol., 35:750–755), Venardos et al. (1980, Enzyme Microb. Technol., 2:112–116), and Sundstrom et al. (1981, Biotechnol. Bioeng., 23:473–485), the contents of each of which are incorporated by reference herein. If the enzymes are in solution, they may be optionally recovered from the product stream for recycle, such as described by Lee et al. (1995, Biotechnol. Bioeng., 45:328–336), the contents of which are also incorporated by reference herein.

The cellulosic material may be treated with the β-1→4 glucanases and β-glucosidase separately (consecutively) or in combination (concurrently). However, to minimize end-product inhibition of the β-1→4 glucanases, the β-glucosidase should be added at an early stage of the reaction thereby preventing the accumulation of cellobiose.

As mentioned hereinabove, this invention may be practiced using lignocellulosic biomass as the substrate. While it is envisioned that this biomass may be treated with the enzymes directly, the rate of hydrolysis and glucose yields will be significantly reduced due to the complex structure of these molecules preventing enzyme access to the cellulose. Consequently, in the preferred embodiment, the lignocellulosic biomass is pretreated to break down the lignin-hemicellulose matrix and thus increase the surface area of the cellulose accessible to the enzymes. The advantages of pretreating lignocellulosic biomass in this manner have been widely recognized in the art, and a variety of different mechanical and chemical pretreatments have been described. Examples of pretreatments which are suitable for use herein include, but are not limited to treatment with dilute or concentrated acid (e.g., HCl, $H_2SO_4$, or $H_3PO_4$) treatment with alkali (e.g., NaOH, or $NH_4OH$), ammonia fiber (or freeze) explosion (AFEX), treatment with organic solvents (e.g., ethanol, methanol, ethylene glycol, butanol, phenol), autohydrolysis by steam explosion, acid steam ($SO_2$) treatment, treatment with hot, compressed liquid water, or pressure cooking. Other mechanical pretreatments which may be used include ball or roll milling, grinding, shearing, or extruding. A detailed review of the mechanisms and conditions for these different pretreatments is described by Weil et al. (1994, Enzyme Microb. Technol., 16:1002–1004) and Wright (1988, ibid), the contents of each of which are incorporated by reference herein. While the mechanisms of action of these pretreatments may be different, all are generally effective to increase the accessible surface area of the cellulose. Depending upon the specific process used, accessible surface area may be increased by removing or disrupting the lignin seal or sheath, solubilizing hemicellulose and/or lignin, disrupting cellulose crystallinity, and/or increasing pore volume. Following completion of many of these hydrolytic pretreatments, the solid residue will typically contain cellulose and lignin, although lignin may be removed in some processes. In contrast, the hemicellulose is usually hydrolyzed to its soluble sugars, including xylose and L-arabinose.

The solid fraction containing the cellulose is retained for enzymatic conversion to glucose as described above. Any solubilized lignin and hemicellulose from the pretreatment may be retained in the substrate during the enzymatic hydrolysis of the cellulose, or in the alternative, they may be removed and recovered for further treatment (Weil et al., 1994, and Wright, 1988, ibid). In one preferred embodiment, the xylose may be fermented to ethanol as described by Wyman (1994, Bioresource Technol., 50:3–16) or Olsson and Hahn-Hagerdal (1996, Enzyme Microbial Technol., 18:312–331), the contents of each of which are incorporated by reference herein.

The glucose produced by enzymatic hydrolysis of the cellulose may be recovered and stored, or it may be subsequently fermented to ethanol using conventional techniques. Many processes for the fermentation of glucose generated from cellulose are well known, and are suitable for use herein. In brief, the hydrolyzate containing the glucose from the enzymatic reaction is contacted with an appropriate microorganism under conditions effective for the fermentation of the glucose to ethanol. This fermentation may be separate from and follow the enzymatic hydrolysis of the cellulose (sequentially processed), or the hydrolysis and fermentation may be concurrent and conducted in the same vessel (simultaneously processed). Details of the various fermentation techniques, conditions, and suitable microorganisms have been described, for example, by Wyman (1994, ibid) and Olsson and Hahn-Hagerdal (1996, ibid).

After completion of the fermentation, the ethanol may be recovered and optionally purified or distilled. Solid residue containing lignin may be discarded or burned as a fuel.

The following examples are intended only to further illustrate the invention and are not intended to limit the scope of the invention which is defined by the claims.

EXAMPLE 1

Materials and Methods

Materials. Cellobiose, microcrystalline cellulose (Sigmacell Type 50), all saccharides, all aryl-glycosides, salicin, molecular weight markers for gel filtration and the glucose detection kit were obtained from Sigma Chemical Co., St. Louis, Mo. Molecular weight markers and precast gels for SDS-PAGE, DEAE Bio-Gel A agarose, Bio Gel A-0.5m gel and an Aminex HPX 87C column for high pressure liquid chromatography (HPLC) were purchased from Bio-Rad Laboratories, Hercules, Calif. Epoxy activated Sepharose 6B was from Pharmacia LKB Biotechnology, Piscataway, N.J. Cello-oligosaccharides ((cellotriose to cellohexaose) prepared by the method of Freer and Detroy (1982, Biotechnol. Lett., 4:453–458) were kindly supplied by R. B. Hespell. Corn bran (Dietfiber NU 20085) was obtained from Lauhoff Grain Company, Danville, Ill. Cytolase 123 was supplied by Genencor International, Rochester, N.Y. Yeast extract was purchased from Difco Laboratories, Detroit, Mich. All other chemicals were of analytical grade.

Yeast strain, medium and culture conditions. The yeast strain (*C. peltata* NRRL Y-21603, also available as NRRL Y-6888) used in this study was obtained from the ARS culture collection, NCAUR, Peoria, Ill. The medium (Slininger et al., 1982, Biotechnol. Bioeng., 23:371–384) used for production of β-glucosidase had the following composition (per L): 10 ml solution A, 10 ml solution B, 100 ml solution C, 10 g yeast extract and 10 g glucose. Solution A was a trace mineral solution having the following ingredients (per L): 1.1 g CaO, 0.4 g ZnO, 5.4 g $FeCl_3 \cdot 6H_2O$, 0.25 g $CuSO_4 \cdot 5H_2O$, 0.24 g $CoCl_2 \cdot 6H_2O$, 0.06 g $H_3BO_3$ and 13 ml concentrated HCl. Solution B (per L) was composed of 10.1 g MgO and 45 ml concentrated HCl. Solution C (per L) contained 64 g urea, 12 g $KH_2PO_4$, and 1.8 g $Na_2HPO_4$. Substrates were sterilized separately. The pH was adjusted to 5.0 with 1M HCl before inoculation. A 250 ml Erlenmeyer flask containing 100 ml medium with glucose (1%) was inoculated with a loopful of cells taken from a stock slant and incubated at 28° C. on a rotary shaker (200 rpm) for 3 days. The shake flasks (250 ml Erlenmeyer flask containing 100 ml medium) were inoculated with 2 ml of this culture and cultivated on a rotary shaker (200 rpm) at 28° C. After 4 days, the cells were removed from the culture broth by centrifugation (18,000×g, 20 min). The resulting supernatant solution was used as the crude enzyme preparation. The organism was grown in 1 L Erlenmeyer flasks containing 500 ml medium using glucose (1%, w/v) as carbon source for the purification of β-glucosidase.

Enzyme assay. β-Glucosidase was routinely assayed using a reaction mixture (1 ml) containing 4 mM p-nitrophenyl β-D-glucoside (pNPβG), 50 mM acetate buffer, pH 5.0 and appropriately diluted enzyme solution. After incubation at 50° C. for 30 min, the reaction was stopped by adding ice-cold 0.5M $Na_2CO_3$ (1 ml) and the color developed as a result of p-nitrophenyl (pNP) liberation was measured at 405 nm. One unit (U) of β-glucosidase corresponds to the release of 1 μmol pNP. $min^{-1}$ in the reaction mixture under these assay conditions.

Purification of β-glucosidase. All steps were carried out at 4° C., unless otherwise stated.

(i) Ammonium sulfate treatment. The culture broth (4.5 L) was concentrated by ultrafiltration with an Amicon stirred cell (Model 202, Amicon, Inc., Beverly, Mass.) equipped with a PM 10 membrane under nitrogen pressure of 20 psi. The concentrated broth (1L) was then treated with ammonium sulfate (80% saturation) and left overnight. The precipitate was collected by centrifugation at 48,000×g for 30 min, dissolved in 50 mM imidazole buffer, pH 6.5 and then dialyzed overnight against the same buffer.

(ii) DEAE Bio-Gel A agarose column chromatography. The dialyzed enzyme solution was loaded on a DEAE Bio-Gel A agarose column (2.5 by 26 cm) pre-equilibrated with 50 mM imidazole buffer, pH 6.5. The column was washed extensively with the same buffer and eluted at first with a gradient of 0–0.5M NaCl in the same buffer (250 ml each) and then with 50 mM imidazole buffer, pH 6.5 plus 0.5M NaCl. The β-glucosidase was eluted as a single active peak. The active fractions were pooled, concentrated by ultrafiltration and dialyzed overnight against 50 mM acetate buffer, pH 5.0.

(iii) Gel filtration on Bio-Gel A-0.5m. The β-glucosidase was further purified by gel filtration on a Bio-Gel A-0.5m column (1.5 by 120 cm) pre-equilibrated with 50 mM acetate buffer, pH 5.0. The enzyme solution in 50 mM acetate buffer, pH 5.0 was applied to the column and eluted with the same buffer. The active β-glucosidase peak fractions were pooled and concentrated by ultrafiltration (PM 10 membrane).

(iv) Cellobiose-Sepharose 6B affinity chromatography. Cellobiose-Sepharose affinity matrix was prepared by coupling cellobiose to epoxy-activated Sepharose 6B by a standard procedure (Affinity Chromatography, Pharmacia Fine Chemicals, Uppsala, Sweden). The β-glucosidase obtained after Bio-Gel A-0.5 m gel filtration was subjected to an affinity chromatography on cellobiose-Sepharose 6B column (2.5 by 6 cm) pre-equilibrated with 50 mM acetate buffer, pH 5.0. The column was washed extensively with 50 mM acetate buffer, pH 5.0 plus up to 2.0M NaCl. The enzyme was finally eluted with the 50 mM imidazole buffer, pH 6.5 plus 2.0M NaCl. The active enzyme fractions were pooled, concentrated by ultrafiltration (PM 10 membrane) and dialyzed against 50 mM acetate buffer, pH 5.0. The dialyzed enzyme solution was used as purified β-glucosidase for subsequent studies.

Analytical methods. Cell growth was monitored by measuring optical density of the culture broth at 660 nm. Protein was estimated by the method of Lowry et al. (1951, J. Biol. Chem., 193:265–275) with bovine serum albumin as standard. Protein in the column effluents was monitored by measuring absorbance at 280 nm. Sodium dodecyl sulfate—polyacrylamide gel electrophoresis (SDS-PAGE) was performed on 12% gels according to the method of Laemmli [1970, Nature (London), 227:680–685]. The molecular weight of the native enzyme was determined by gel filtration on Bio-Gel A-0.5 m, as described by Andrews (1965, Biochem J., 91:595–606), using bovine serum albumin (66,000), ovalbumin (45,000), carbonic anhydrase (31,000), trypsin inhibitor (21,500), and lysozyme (14,400) as standard proteins. Glucose was determined by the glucose oxidase-peroxidase-o-dianisidine (GOPOD) method of Hugget and Nixon (1957, Biochem J., 6:12–19). The $K_m$ and $V_{max}$ values were determined by the double-reciprocal plot method of Lineweaver-Burk (1934, J. Amer. Chem. Soc., 56:658–666) using KINET software program. Sugar analysis was performed by HPLC on an Aminex 87C column (300 by 7.8 mm) heated to 85° C. with water as the eluent (flow rate, 0.6 ml/min). Peaks were detected by refractive index, and identified and quantitated by comparison to retention times of authentic cellobiose and glucose standards.

Results

Production of β-glucosidase. The effect of a variety of carbon sources on growth and β-glucosidase synthesis by *C. peltata* in shake flasks is presented in Table 1. The yeast was grown in liquid culture with 1% (w/v) substrate at 28° C. for 4 days. It produced β-glucosidase on all substrates. Highest β-glucosidase activity (117 mU/ml) was obtained in xylose grown whole culture broth. Glucose was a good growth substrate for production of β-glucosidase. About 55–89% of β-glucosidase activity was found in the culture supernatant, depending on the carbon source used. The time course of β-glucosidase production by the yeast grown on glucose (1%) was studied. Enzyme production increased up to 4 days after which it decreased gradually (FIG. 1). The effect of glucose (up to 20%) on growth and production of β-glucosidase was also investigated. Enzyme production increased slightly with glucose concentration up to 4% and then decreased gradually with the increase of glucose concentration in the medium (Table 1). However, at higher glucose concentration, the enzyme production was 88–100% extracellular.

Purification of β-glucosidase. Table 2 summarizes the results of the purification procedures of an extracellular β-glucosidase from the culture supernatant of C. peltata grown on glucose. The enzyme was purified 1800-fold to homogeneity with an overall enzyme yield of 36% and a specific activity of 108 U. mg$^{-1}$ protein. Only one form of β-glucosidase was detected during the purification steps. No change in cellobiose hydrolyzing activity was observed among the pNPβG active enzymes at each purification step in comparison with that of the crude enzyme. SDS-PAGE analysis of the purified enzyme indicated the presence of a single band when stained with Coomassie Brilliant Blue.

Characterization of β-glucosidase.

Figure 2:
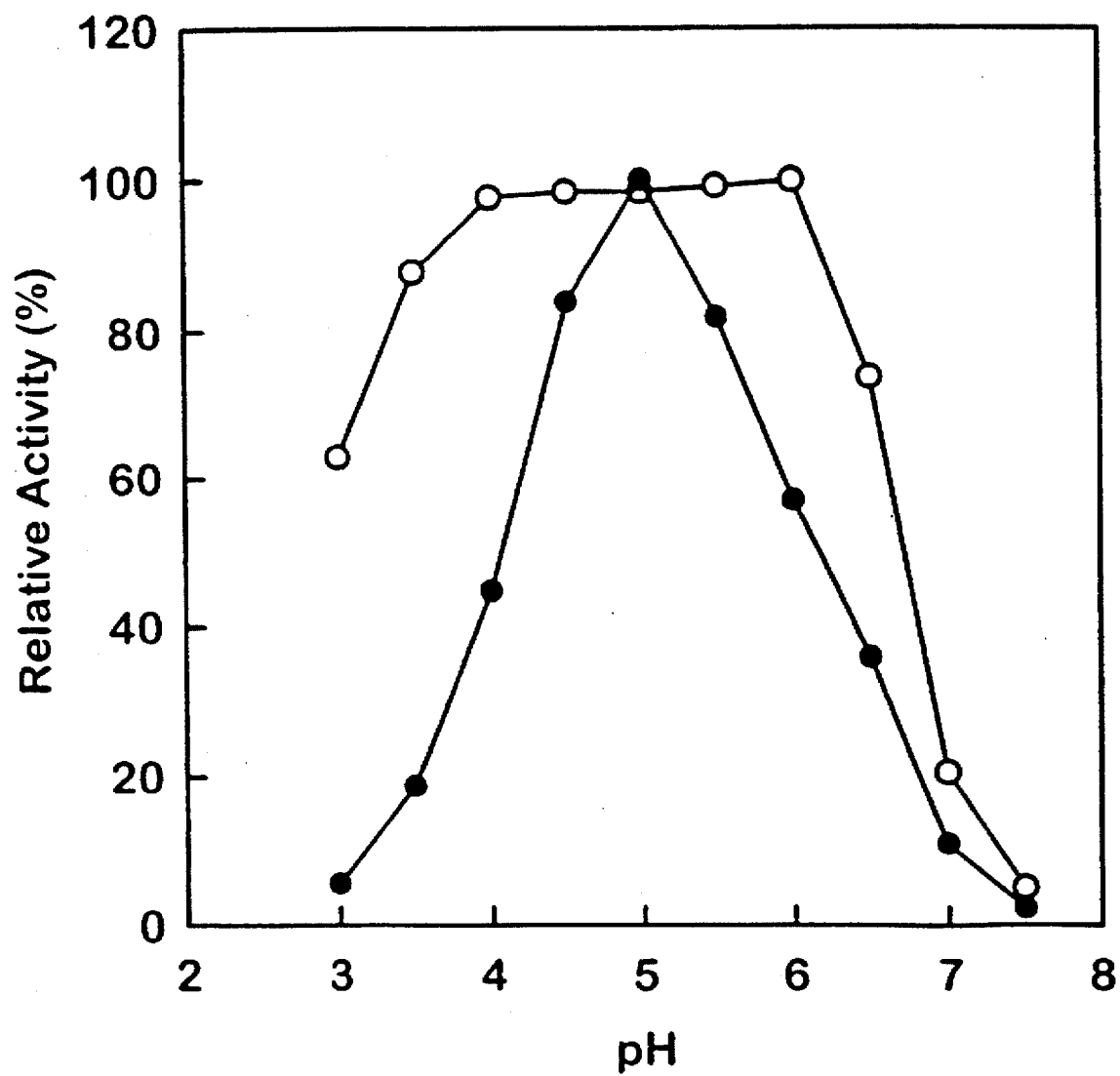
FIG. 2. Effect of pH on stability and activity of purified β-glucosidase from *C. peltata* Y-21603. For stability, the enzyme solutions in 50 mM buffer at various pH values were incubated for 30 min at 40° C. After adjustment of pH, the residual activity was assayed by the standard method. For activity, the enzyme activity was assayed by the standard assay method by changing the buffer to obtain the desired pH. Buffer used, citrate-phosphate (pH 3.0–7.5). Enzyme used, 0.03 U/ml. Symbols: ○, stability; ●, activity.
Figure 3:
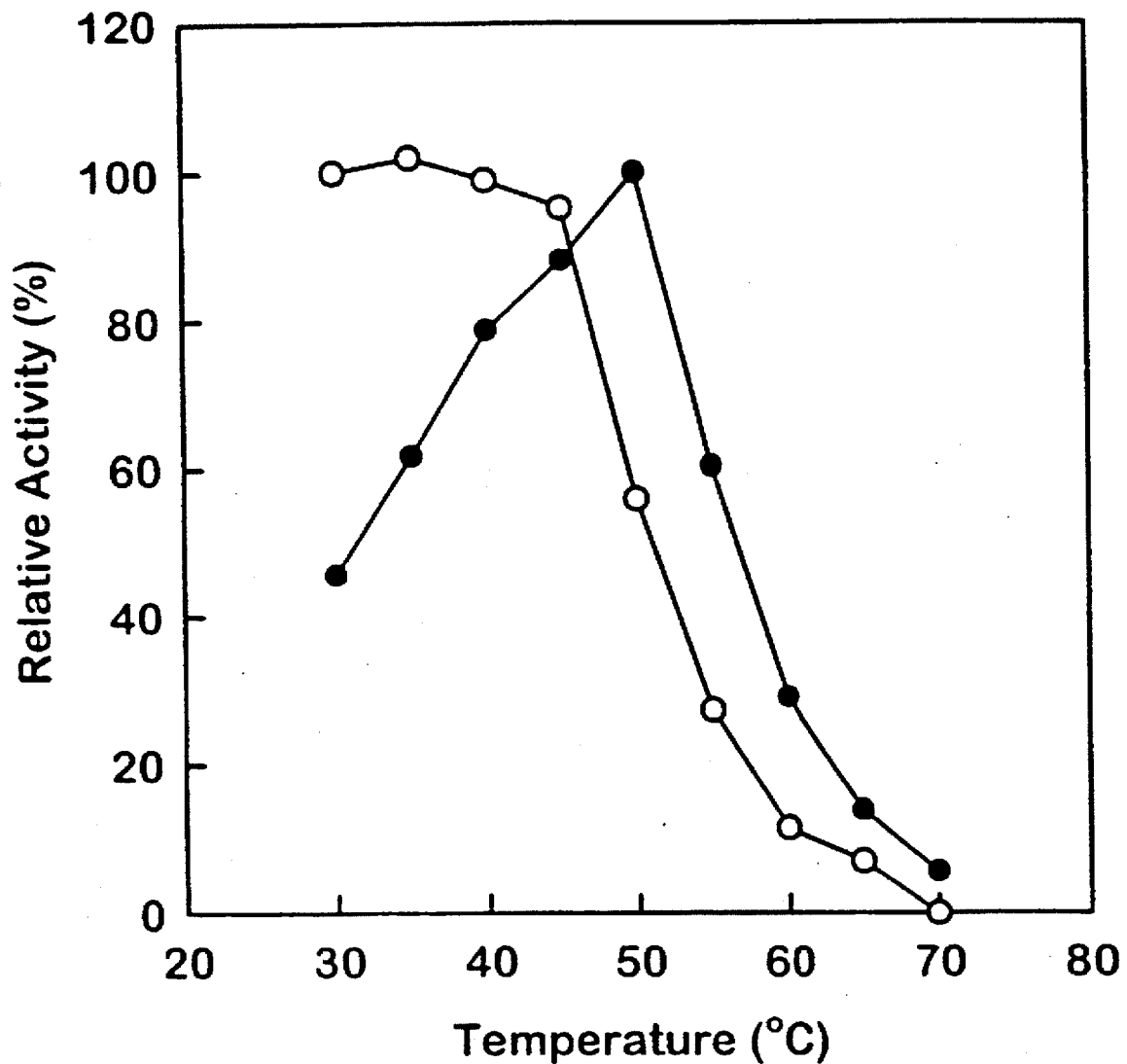
FIG. 3. Effect of temperature on stability and activity of purified β-glucosidase from *Candida peltata* Y-21603. For stability, the enzyme solution in acetate buffer (50 mM, pH 5.0) was incubated for 30 min at various temperatures, and then the residual enzyme activities were assayed. For activity, the enzyme was assayed at various temperatures by the standard assay method. Enzyme used, 0.03 U/ml. Symbols: ○, stability; ●, activity.

Molecular weight. The molecular weight of the native β-glucosidase estimated by gel filtration on Bio-Gel A-0.5 m was 43,500 and by SDS-PAGE analysis about 43,000, suggesting that the β-glucosidase was a monomeric protein.

pH and temperature dependence. The pH stability and activity curves for the β-glucosidase are shown in FIG. 2. The enzyme was fairly stable at pH 4.0–6.0 (30 min at 40° C.) with 62% activity at pH 3.0 and 21% activity remaining at pH 7.0. It exhibited an optimal activity at pH 5.0 with 45% and 57% activity at pH 4.0 and 6.0, respectively. The effects of temperature on the stability and activity of the purified β-glucosidase are shown in FIG. 3. The enzyme in 50 mM acetate buffer, pH 5.0 (0.03 U/ml; 0.28 µg/ml) was fairly stable up to 45° C. for 30 min. It was inactivated upon incubation at 70° C. for 30 min. The β-glucosidase (1.2 mg/ml) retained its full activity at 4° C. after storage in 50 mM acetate buffer (pH 5.0) for more than 4 months. The enzyme displayed maximal activity at 50° C.

Substrate specificity and kinetic analysis. Relative rates of hydrolysis of various substrates by the purified β-glucosidase were studied. The enzyme could hydrolyze pNPβG and cellobiose effectively. Salicin was hydrolyzed at 34% of that of cellobiose. The purified enzyme had very little (<5%) or no activity on lactose, maltose, sucrose and trehalose. It also had no or very little activity on p-nitrophenyl-α-D-glucoside, p-nitrophenyl-β-D-xyloside, p-nitrophenyl-β-D-cellobioside, p-nitrophenyl-α-L-arabinofuranoside, and p-nitrophenyl-β-D-glucuronide (<5%). p-Nitrophenyl-β-D-galactoside was hydrolyzed at 6% of that of pNPβG. The reaction kinetics of the purified enzyme were determined from Lineweaver-Burk plots using pNPβG and cellooligosaccharides (cellobiose to cellohexaose) as substrates under optimal conditions (pH 5.0 and 50° C.). The enzyme had apparent K$_m$ values of 2.3, 66, 39, 35, 21, 18 mM and V$_{max}$ values of 221, 75, 32, 16, 8, and 5 µmol.min$^{-1}$.mg$^{-1}$ protein for the hydrolysis of pNPβG, cellobiose, cellotriose, cellotetraose, cellopentaose and cellohexaose, respectively.

Figure 4:
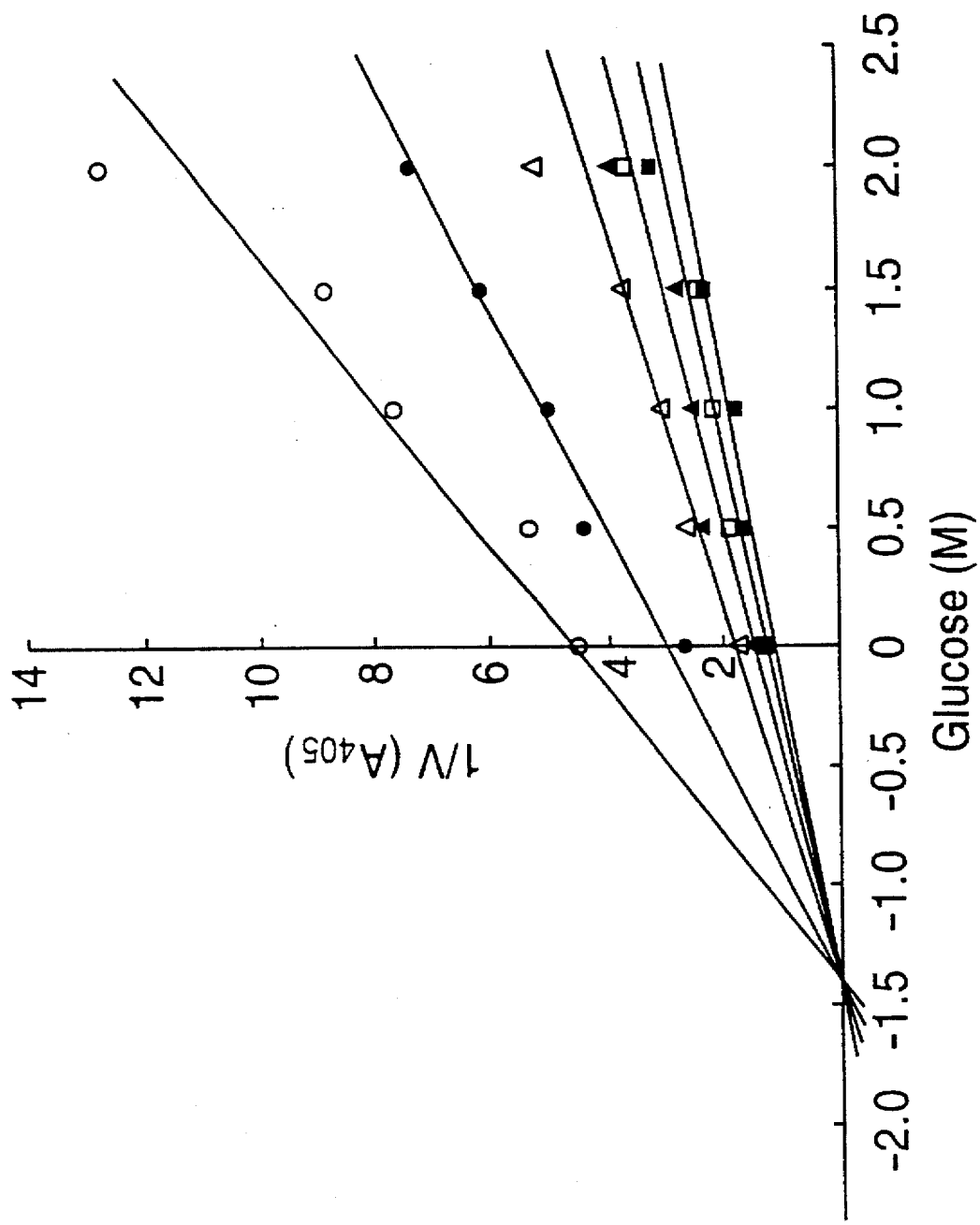
FIG. 4. Dixon plot of inhibitory effect of glucose on p-nitrophenyl β-D-glucoside hydrolysis by purified β-glucosidase from *Candida peltata* Y-21603. Reaction time was 15 min at pH 5.0 and 50° C. Enzyme used, 39 mU/ml. pNPβG used: ○, 0.4 mM; ●, 0.8 mM; ▲, 1.2 mM; △, 1.6 mM; □, 2.0 mM; ■, 2.4 mM.

Inhibition by glucose cellobiose and other sugars. The study of inhibition by glucose was performed with pNPβG as substrate. Glucose acted as competitive inhibitor of pNPβG hydrolysis with an inhibition constant (K$_i$) of 1.4M (252 mg/ml) obtained at the intersection of the lines on the Dixon plot analysis (FIG. 4). Galactose, mannose, arabinose, fructose, xylose (each at 56 mM), sucrose and lactose (each at 29 mM) did not inhibit the β-glucosidase activity. Substrate inhibition was not observed at all with either 40 mM pNPβG or 15% cellobiose.

Inhibitors and activators. The effect of selective inhibitors or activators on β-glucosidase activity was examined. The enzyme was not dependent on Ca$^{2+}$, Mg$^{2+}$, Mn$^{2+}$ (each at 5 mM) or Co$^{2+}$ (0.5 mM) for activity. Enzyme activity was not affected by ethylenediaminetetraacetate (EDTA, 10 mM), dithiothreitol (DTT, 10 mM) or by p-chloromercuribenzoic acid (pCMB, 0.2 mM). Ethanol at optimal concentration had very little stimulating effect on the initial β-glucosidase activity. The pNPβG hydrolysis by the enzyme at pH 5.0 and 50° C. was increased by 11% (30 min reaction) at 0.75% (v/v) ethanol after which the activity dropped.

Figure 5:
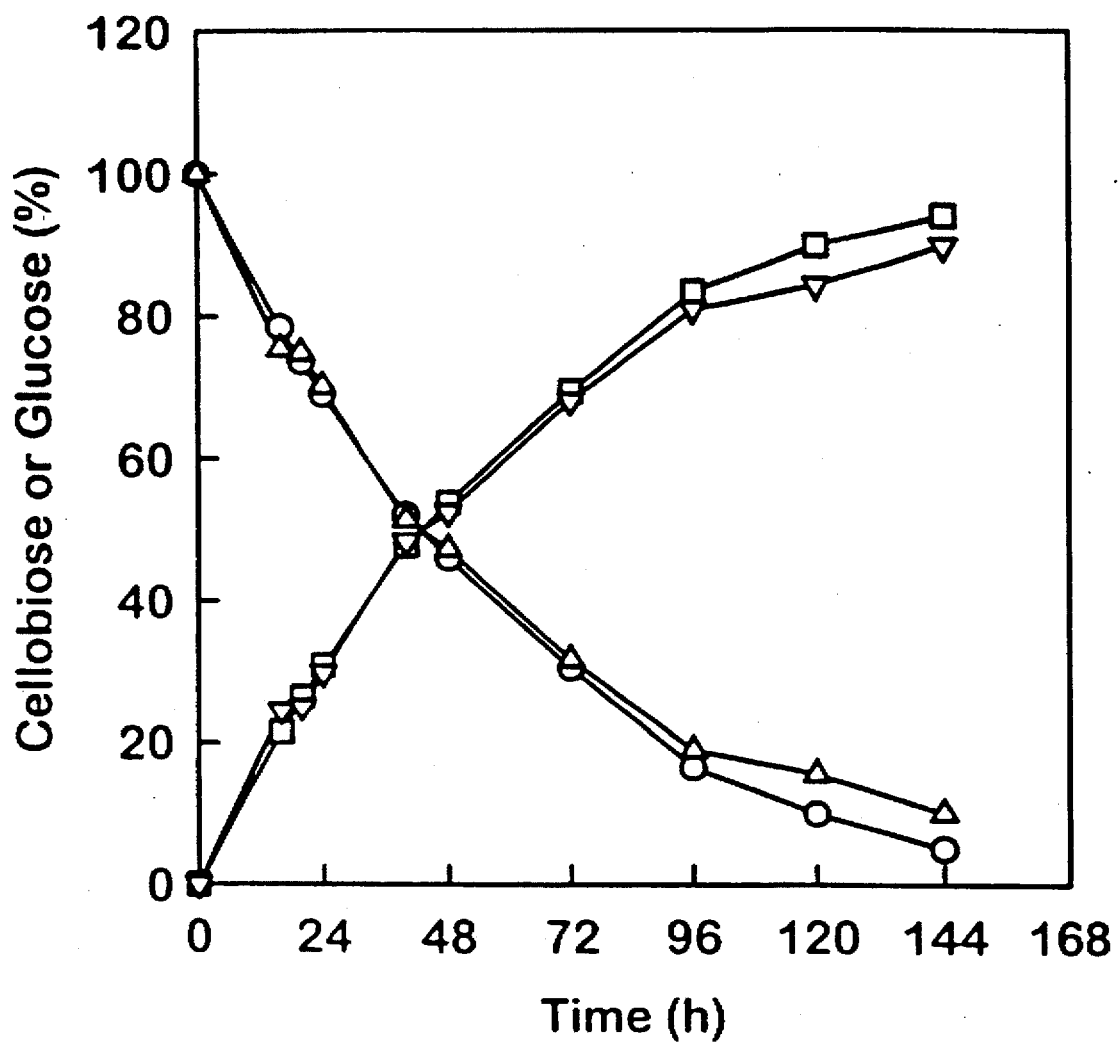
FIG. 5. Time course of cellobiose (10%, w/v) hydrolysis by purified β-glucosidase (1.5 U/ml) from *Candida peltata* Y-21603 in the absence and presence of glucose (6%, w/v) at pH 5.0 and 50° C. Symbols: (○), cellobiose only; (□), glucose formed from cellobiose, (△), cellobiose with glucose; (▽), glucose formed from cellobiose in the presence of glucose.

Cellobiose hydrolysis. FIG. 5 shows the rates of cellobiose (10%, w/v) hydrolysis performed by purified β-glucosidase (1.5 U/ml) both in the presence and absence of glucose (6%, w/v). Both cellobiose degradation and glucose production were quantified by using HPLC. Glucose was detected as the only reaction product from cellobiose during the course of the reaction. The enzyme was able to function very well in the presence of glucose and hydrolyzed about 90% cellobiose to glucose in 144 h.

Synergism with cellulase. The effect of purified β-glucosidase (0.4 U/ml) supplementation on microcrystalline cellulose (Sigmacell Type 50, 2%, w/v) hydrolysis at pH 5.0 and 50° C. by a commercial cellulase preparation (Cytolase 123 cellulase, 5 U/ml; β-glucosidase, 0.45 U/ml) was examined by comparing the nature and quantity of the soluble products formed in the absence and presence of the enzyme. The reaction products were analyzed by HPLC. After 24 h, there was an 8.3% increase in the production of glucose from Sigmacell by the cellulase preparation supplemented with the β-glucosidase. The β-glucosidase itself had no activity on microcrystalline cellulose. Thus, the β-glucosidase from C. peltata had synergistic interaction with cellulase to increase the efficiency of glucose production from cellulose.

Discussion

To our knowledge, these findings represent the first report on the production, purification and characterization of a yeast β-glucosidase having such a high tolerance to glucose (K$_i$=1.4M). The level of production of β-glucosidase by C. peltata NRRL Y-21603 depended on the carbohydrate source (Table 1). It is interesting that highest enzyme production (117 mU/ml) was observed in xylose grown culture broths. Provision of cellobiose as the carbohydrate source was not at all required for enzyme production. The yeast produced β-glucosidase when grown on all carbon source examined. Thus, the β-glucosidase of C. peltata seemed to be a constitutive enzyme, regardless of the presence and absence of cellobiose. The yeast produced β-glucosidase significantly even when grown on 20% glucose. It also produced ethanol from glucose. The decrease in enzyme activity in the culture broth when the yeast was grown at a higher glucose concentration may be due to the alcohol produced by the yeast which inhibited the enzyme activity when assayed with the culture broth. This indicates that the enzyme synthesis might not be repressed by glucose.

The majority of the β-glucosidase activity was extracellular. An extracellular β-glucosidase was purified 1800-fold from the glucose grown cell-free culture broth by a four-step procedure involving ammonium sulfate treatment, DEAE Bio-Gel A agarose ion exchange chromatography, Bio-Gel A-0.5 m gel filtration and affinity chromatography on cellobiose-Sepharose 6B (Table 2). The enzyme was tightly adsorbed onto the affinity matrix, and was eluted only by changing the buffer, changing the pH, and adding strong salt (2M NaCl) concentration. Only one active form of enzyme was detected during the purification procedures. Multiple forms of β-glucosidase have been found in the culture broth of a variety of microbes (Chen et al., 1994, Appl. Environ. Microbiol., 60:64–70, Gueguen et al., ibid, Li and Calza, 1991, Enzyme Microb. Technol., 13:622–628, Lymer and Renganathan, 1995, Appl. Environ. Microbiol., 61:2976–2980, Ozaki and Yamada, 1992, Agric. Biol. Chem., 55:979–987, and Schmid and Wandrey, ibid). The specific activity of β-glucosidase from *C. peltata* was 108 U/mg protein under optimal conditions (at pH 5.0 and 50° C.). The specific activity of purified β-glucosidases from other microorganisms ranges from 5 to 979 U/mg protein (Ait et al., 1982, J. Gen. Microbiol., 128:569–577, Freer, 1985, Arch. Biochem. Biophys., 243:515–522, Kwon et al., 1992, FEMS Microbiol. Lett., 97:149–154, Li and Calza, ibid, Waldron et al., 1986, Appl. Microbiol. Biotechnol., 24:477–486).

The molecular weight (43,000) of the β-glucosidase from *C. peltata* is similar to that of the extracellular β-glucosidases from *Clostridium thermocellum* (MW 43,000), *Monilia sp.* (46,600), *Piromyces sp.* (45,000), *T. koningii* (39,800) and intracellular β-glucosidase from *S. thermophile* (40,000) (Ait et al., ibid, Berry and Dekker, 1986, Carbohydr. Res., 157:1–12, Bhat et al., 1993, J. Gen. Microb., 139:2825–2832, Teunissen et al., 1992, Arch. Microbiol., 158:276–281, Wood and McCrae, 1980, J. Gen Microb., 128:2973–2982). Molecular weights of β-glucosidases from various microbial sources vary from 39,800 to 480,000 (Dekker, 1981, J. Gen. Microbiol., 127:177–184, Saha et al., 1995, ibid, Teunissen et al., ibid, Wood and McCrae, ibid). The optimal activity of the purified enzyme was observed at pH 5.0 and 50° C. (FIGS. 2 and 3). The optimal pH and temperature of β-glucosidases from various microbial sources ranges between pH 3–7 and 40°–105° C. (Coughlan, ibid, Kengen et al., 1993, Eur. J. Biochem., 213:305–312, Saha et al., ibid, Woodward and Wiseman, ibid).

Glycosidases may be divided into three groups on the basis of substrate specificity: (i) aryl-β-glucosidase (which hydrolyzes exclusively aryl-β-glucosides), (ii) cellobiase (which hydrolyzes cellobiose and short chain cellodextrins only), and (iii) broad specificity β-glucosidases (which show activity on both substrate types). The later type is the most commonly observed group in cellulolytic microorganisms (Chen et al., ibid, Gueguen et al., ibid, Paavilainen et al., 1993, Appl. Environ. Microbiol., 59:927–932, Painbeni et al., 1992, J. Bacteriol., 174:3087–3091, Saha et al., 1995, ibid, Schmid and Wandrey, ibid, Woodward and Wiseman, ibid). The β-glucosidase from *C. peltata* is a broad specificity type as it hydrolyzed cellobiose, cellooligosaccharides and pNPβG. The enzyme had very little β-xylosidase, L-arabinofuranosidase and β-glucuronidase activity (less than 5% of that of β-glucosidase). It hydrolyzed p-nitrophenyl-β-D-galactoside at 6% of that of pNPβG. Although there are a few exceptions (Ait et al., ibid, Freer, 1985, ibid, Ozaki and Yamada, ibid, Waldron et al., ibid, Wright et al., 1992, Appl. Environ. Microbiol., 58:3455–3465), the competitive inhibition of β-glucosidase by glucose is a quite common phenomenon (Gueguen et al., ibid, Painbeni et al., ibid, Saha et al., 1995, ibid, Woodward and Wiseman, ibid). Most microbial enzymes show inhibition constants ($K_i$) of 0.6–8 mM for glucose (Ozaki and Yamada, ibid). The β-glucosidases from *Sporotrichum thermophile, Monilia sp., F. oxysporum, Neocallimastrix frontalis, B. cinerea* and *Streptomyces sp.* strain QM-B814 were competitively inhibited by glucose with $K_i$s of 0.5, 0.67, 2.05, 5.5, 10.5, and 65 mM, respectively (Bhat et al., ibid, Christakopoulos et al., 1994, Eur. J. Biochem., 224:379–385, Dekker, ibid, Gueguen et al., ibid, Li and Calza, ibid, Perez-Pons et al., 1994, Eur. J. Biochem., 223:557–565). FIG. 4 shows that glucose caused competitive inhibition of the β-glucosidase of *C. peltata* with a $K_i$ of 1.4M (252 mg/ml) which indicates that the enzyme is highly tolerant to glucose. Glucose inhibited the β-glucosidase catalyzed reaction of *T. viride* cellulase in a mixed inhibition pattern with a competitive character (Montero and Romeu, 1992, Appl. Microbiol. Biotechnol., 38:350–353). The inhibition of β-glucosidase from *P. furiosus* by glucose was almost negligible with a $K_i$ of 300 mM (Kengen et al., ibid). Aryl-β-glucosidase of Trichoderma was totally inhibited by 1% glucose and *Microbispora bispora* aryl-β-glucosidase was 35, 66 and 79% inhibited by 10, 20 and 30% glucose, respectively (Waldron et al., ibid). A cloned β-glucosidase (BglB) from *M. bispora* was also activated two to three-fold in the presence of 2–5% (0.1–0.3M) glucose and did not become inhibited until the glucose concentration reached about 40% (Wright et al., ibid). One β-glucosidase from *Streptomyces sp.* was activated two-fold by 1.8% glucose and another one from the same strain was 50% inhibited by 18% glucose (Ozaki and Yamada, ibid). Recently, Perez-Pons et al. (1995, Biochim. Biophys. Acta, 1251:145–153) reported that glucose in the range 0.45–3.6% (25–200 mM) enhanced the rate of pNPβG hydrolysis by a β-glucosidase isolated from Streptomyces sp.

None of the divalent cations tested had significant stimulatory or inhibitory effects on β-glucosidase activity. Strong inhibition of β-glucosidases is generally observed with p-chloromercuribenzoate (pCMB), a thiol-specific inhibitor (Ait et al., ibid, Perez-Pons et al., 1995, ibid). However, the β-glucosidase activity from *C. peltata* was unaffected by pCMB. This suggests that sulfhydryl groups are not involved in the catalytic center of the enzyme. The β-glucosidases from *P. furiosus* and *A. pullulans* are also unaffected by thiol-specific inhibitors (Kengen et al., ibid, Saha et al., 1994, ibid). Substrate inhibition by cellobiose is a common property of β-glucosidase from *Trichoderma sp.* and other microorganisms (Chen et al., ibid, Perez-Pons et al., 1994, ibid, Saha et al., 1995, ibid, Schmid and Wandrey, ibid, Teunissen et al., ibid). Cellobiose strongly inhibited its own hydrolysis by β-glucosidase from *Pyromyces sp.* at concentrations above 0.2 mM (Teunissen et al., ibid). The inhibition constant ($K_i$) for cellobiose was 0.62 mM. The β-glucosidase from *Orpinomyces sp.* was inhibited by cellobiose at a concentration higher than 1.5 mM (Chen et al., ibid). The β-glucosidase from *A. pullulans* was not inhibited by 20 mM pNPβG or 6% cellobiose (Saha et al., 1994, ibid). The β-glucosidase from *C. peltata*, however, was not inhibited at all by either 40 mM pNPβG or 15% cellobiose. This indicates that the enzyme is very tolerant to substrate. Activation of enzyme by ethanol was observed for β-glucosidases from *F. oxysporum* (Christakopoulos et al., ibid), *Dekkera intermedia* (Blondin et al., 1983, Eur. J. Microbiol. Biotechnol., 17:1–6) and *A. pullulans* (Saha et al., 1994, ibid) which may be due to glucosyl-transferase activity of the enzyme (Pemberton et al., 1980, Can. J. Chem. Eng., 58:723–729). The β-glucosidase could preferentially utilize alcohols rather than water as acceptors for the glycosyl moiety during catalysis of pNPβG resulting in elevated reaction rates which suggests that ethanol increases the hydrolysis rate of pNPβG by acting as an acceptor molecule for glucose (Pemberton et al., ibid, Saha et al., 1994, ibid). Ethanol increased the activity of β-glucosidase from *F. oxysporum* 1.5 fold (Christakopoulos et al., ibid). In comparison, the initial activity of β-glucosidase from *C. peltata* was stimulated only 11% by ethanol at an optimal concentration (0.75 %, v/v). This result suggests that the β-glucosidase from *C. peltata* may have little transglucosylation activity. This property is advantageous for the use of the enzyme in the simultaneous saccharification and fermentation of cellulosic materials to ethanol.

The data in FIG. 5 demonstrates that the β-glucosidase from *C. peltata* hydrolyzed cellobiose (10%) in presence of glucose (6%) very well. No transglucosylation product was detected by HPLC analysis during the course of the reaction which also indicates that the enzyme may not have any transglucosylation activity. The enzyme exhibited synergistic interaction with a commercial cellulase preparation to increase the efficiency of glucose production from microcrystalline cellulose by converting cellobiose to glucose.

In conclusion, the ease of yeast culture, high level of enzyme production on glucose, high activity of the β-glucosidase on cellobiose and its very high cellobiose (substrate) and novel glucose (product) tolerance are particularly favorable for its application in the enzymatic hydrolysis of cellulose to glucose at a desirable moderate temperature.

EXAMPLE 2

The β-glucosidase of *C. peltata* produced in Example 1 was compared with β-glucosidases of forty-seven selected yeasts for inhibition of activity by glucose. The process was described in Saha and Bothast (1996, Biotechnol. Letters, 18:155–158), the contents of which are incorporated by reference herein.

The strains used obtained from the ARS Culture Collection, National Center for Agricultural Utilization Research, Peoria, Ill. These strains with their NRRL numbers were: *Candida auringiensis* Y-11848, *C. buinensis* Y-11706, *C. chilensis* Y-17141, *C. conglobata* Y-1504, *C. dendronema* Y-7781, *C. diddensiae* Y-7589, *C. entomaea* Y-7785, *C. entomophila* Y-7783, *C. ernobii* Y-12940, *C. hellenica* Y-17319, *C. insectorum* Y-7787, *C. membranaefaciens* Y-2089, *C. mogii* Y-17032, *C. naeodendra* Y-10942, *C. peltata* Y-21603, *C. shehatae* Y-17029, *C. silvanorum* Y-7782, *C. silvicultrix* Y-7789, *C. succiphila* Y-11998, *C. tenuis* Y-1498, *Debaryomyces hansenii* Y-7426, *D. nepalensis* Y-7108, *D. yamadae* Y-11714, *Geotrichum fermentans* Y-1492, *Kluyveromyces marxianus* Y-1195, *Pichia angusta* Y-2214, *P. bimundalis* Y-5543, *P. burtonii* Y-1933, *P. bovis* YB-4184, *P. capsulata* Y-1842, *P. ciferrii* Y-1031, *P. etchellsii* Y-7121, *P. haplophila* Y-7860, *P. holstii* Y-2155, *P. guilliermondii* Y-2075, *P. kodamae* Y-17234, *P. methanolica* Y-7685, *P. methylovora* Y-17250, *P. mexicana* Y-11818, *P. mississippiensis* YB-1294, *P. nakazawae* Y-7903, *P. philogaea* Y-7813, *P. pinus* Y-11528, *P. scolytii* Y-5512, *P. stipitis* Y-7124, *P. sydowiorum* Y-7130, *P. trehalophila* Y-6781 and *Saccharomycopsis capsularis* Y-17639.

The medium used for production of β-glucosidase was the same as described in Example 1. A 125-ml Erlenmeyer flask containing 50 ml the medium with L-arabinose (50 g/L, Sigma Chemical Company, St. Louis, Mo.) was inoculated with a loopful of cells taken from a stock slant and incubated at 28° C. on a rotary shaker (200 rpm) for 4 days.

Culture supernatant was assayed for β-glucosidase activity was assayed using p-nitrophenyl-β-D-glucoside (pNPβG) as substrate by the procedure described in Example 1. Glucose was estimated by the glucose oxidase-peroxidase-o-dianisidine method of Hugget and Nixon (ibid).

Results

Production of β-glucosidase. All yeast strains produced extracellular β-glucosidase. The activity level varied with each yeast strain. Highest extracellular β-glucosidase activity was 2.59 U/ml culture broth produced by *P. kodamae*, followed by *P. mississippiensis* (2.53 U/ml), *P. etchellsii* (0.87 U/ml), *P. holstii* (0.50 U/ml) and *P. capsulata* (0.86 U/ml). Debaryomyces strains were low producers of β-glucosidase (8–29 mU/ml culture broth). *C. mogii* produced lowest β-glucosidase (1 mU/ml).

Inhibition of β-glucosidase by glucose. Inhibition of β-glucosidase from each yeast strain by various concentrations (0–30%, w/v) of glucose was tested using pNPβG as substrate. Each enzyme preparation reacted differently in the presence of glucose. β-glucosidases from some yeast strains were strongly inhibited (decrease in activity expressed as % of that in the absence of glucose), even by 1.2% (w/v) glucose. Some of these yeast strains were *G. fermentans* (56%), *S. capsularis* (50%), *C. silvicultrix* (45%), *C. hellinica* (38%), *P. mexicana* (35%), *P. bimundalis* (34%), *P. kodamae* (31%), *C. entomaea* (30%), *P. angusta* (27%), *C. diddensiae* (27%) and *P. burtonii* (24%). β-Glucosidases from some other yeast strains were not at all or very little affected by 1.2% glucose. These yeast strains were *C. silvanorum* (0%), *D. hansenii* (0%), *P. methylovora* (1%), *D. nepalensis* (1%), *P. nakazawae* (1%), *P. methanolica* (2%), *P. etchellsii* (2%), *C. auringiensis* (3%), *C. ernobii* (4%), *P. haplophila* (5%), *P. pinus* (5%), *P. guilliermondii* (5%), *P. ciferrii* (6%), *C. chilensis* (6%), *D. yamadae* (6%), *C. naeodendra* (76), *P. holstii* (7%) and *P. stipitis* (7%). Some other β-glucosidase activities were even stimulated by 1.2% glucose. These yeast strains were *C. peltata* (6%), *C. insectorum* (8%), *C. shehatae* (6%), *P. bovis* (3%) and *K. marxianus* (2%).

The results of the fifteen strains exhibiting highest tolerance to glucose are shown in Table 3. Of the strains examined, crude β-glucosidase from *C. peltata* exhibited the greatest stimulation of activity at glucose concentrations of 3 and 12%. At 30% glucose, β-glucosidase activity was only reduced 25% relative to the activity in the absence of glucose.

It is understood that the foregoing detailed description is given merely by way of illustration and that modifications and variations may be made therein without departing from the spirit and scope of the invention.

TABLE 1

Growth and β-glucosidase production by *Candida peltata* Y-21603 on various substrates[a]

| Carbon source | Growth | β-Glucosidase (mU/ml culture) | |
|---|---|---|---|
| (%, w/v)[b] | ($A_{660}$) | Whole broth | Supernatant |
| Control (no carbon source) | 2.4 | 18 | 16 |
| Corn bran (1) | —[c] | 23 | 16 |
| Sigmacell type 50 (1) | — | 18 | 16 |
| Oat spelt xylan (1) | — | 19 | 16 |
| Carboxymethyl cellulose (1) | 3.2 | 17 | 14 |
| Soluble starch (1) | 5.2 | 19 | 11 |
| Maltose (1) | 9.3 | 81 | 62 |
| Cellobiose (1) | 8.7 | 79 | 62 |
| Lactose (1) | 2.5 | 28 | 22 |

TABLE 1-continued

Growth and β-glucosidase production by *Candida peltata* Y-21603 on various substrates[a]

| Carbon source (%, w/v)[b] | Growth ($A_{660}$) | β-Glucosidase (mU/ml culture) | |
|---|---|---|---|
| | | Whole broth | Supernatant |
| Sucrose (1) | 9.0 | 89 | 49 |
| L-Arabinose (1) | 9.4 | 98 | 74 |
| Xylose (1) | 11.3 | 117 | 85 |
| Glucose (1) | 10.7 | 93 | 79 |
| Glucose (2) | 13.7 | 97 | 78 |
| Glucose (4) | 13.3 | 111 | 98 |
| Glucose (8) | 9.7 | 88 | 88 |
| Glucose (12) | 7.9 | 75 | 75 |
| Glucose (20) | 7.3 | 49 | 47 |

[a]Cultures were grown in 250 ml Erlenmeyer flasks containing 100 ml medium at 28° C. for 4 days. Initial pH of the medium was 5.0 before inoculation.
[b]The number in parenthesis indicates the percent of each substrate used.
[c]—, not determined.

TABLE 2

Purification of β-glucosidase from *Candida peltata* Y-21603

| Step | Total protein (mg) | Total activity (U) | Specific activity (U/mg protein) | Recovery (%) | Purification fold |
|---|---|---|---|---|---|
| Culture supernatant | 7,094 | 392 | 0.06 | 100 | 1 |
| Ultrafiltration | 2,215 | 365 | 0.16 | 93 | 2.7 |
| Ammonium sulfate | 175 | 286 | 1.6 | 73 | 27 |
| DEAE Bio-Gel A agarose | 7.8 | 231 | 29.6 | 59 | 494 |
| Bio-Gel A-0.5m | 2.3 | 163 | 70.9 | 42 | 1182 |
| Cellobiose-Sepharose | 1.3 | 141 | 108 | 36 | 1800 |

TABLE 3

Effect of glucose on extracellular β-glucosidase activity of selected yeasts.

| Yeast strain | β-Glucosidase (mU/ml) | Inhibition of activity (%)[a] Glucose (%, w/v) | | |
|---|---|---|---|---|
| | | 3 | 12 | 30 |
| *Candida chilensis* | 36 | 9 | 22 | 45 |
| *Candida denaronema* | 33 | 18 | −7 | 33 |
| *Candida ernobii* | 7 | 5 | 18 | 39 |
| *Candida insectorum* | 17 | −9 | 10 | 47 |
| *Candida membranaefaciens* | 14 | 12 | 21 | 40 |
| *Candida naeodendra* | 166 | 14 | 34 | 46 |
| *Candida peltata* | 73 | −33 | −13 | 25 |
| *Candida shehatae* | 13 | −2 | 2 | 30 |
| *Debaryomyces hansenii* | 9 | 1 | 12 | 38 |
| *Debaryomyces nepalensis* | 8 | 7 | 18 | 37 |
| *Debaryomyces yamadae* | 29 | 11 | 27 | 49 |
| *Kluyveromyces marxianus* | 18 | 8 | 25 | 48 |
| *Pichia guilliermondii* | 15 | 4 | 19 | 47 |
| *Pichia methanolica* | 44 | 0 | 3 | 22 |
| *Pichia nakazawae* | 90 | 17 | 3 | 28 |

[a]Decrease in activity expressed as % of that in the absence of glucose. Values are from duplicate experiments for each enzyme preparation.

We claim:

1. A glucose tolerant and cellobiose tolerant β-glucosidase produced by *Candida peltata* NRRL Y-21603 and which is isolated from cells thereof, wherein said β-glucosidase is effective for hydrolysis of cellobiose to glucose.

2. The β-glucosidase of claim 1 which is substantially pure.

3. A composition comprising the β-glucosidase of claim 1 free from cells of said *Candida peltata* NRRL Y-21603 and an inert carrier.

4. A method for converting cellulosic material to glucose comprising:

a. contacting a cellulosic material with a β-1→4 glucanase in an amount and under conditions effective to produce cellobiose from cellulose; and b. contacting said cellobiose with a β-glucosidase produced by *Candida peltata* NRRL Y-21603 in an amount and under conditions effective for hydrolyzing said cellobiose to glucose.

5. The method as described in claim 4 wherein said cellulosic material is contacted with said β-1→4 glucanase and said β-glucosidase simultaneously.

6. The method as described in claim 4 wherein said β-1→4 glucanase is selected from the group consisting of endo-1,4-β-glucanase, exo-1,4-β-glucanase, and mixtures thereof.

7. The method as described in claim 6 wherein said β-1→4 glucanase is a mixture of said endo-1,4-β-glucanase and said exo-1,4-β-glucanase.

8. The method as described in claim 4 wherein said cellulosic material comprises a lignocellulosic biomass.

9. The method as described in claim 8 further comprising subjecting said lignocellulosic biomass to a pretreatment to increase the accessible surface area of cellulose, prior to said contacting with said β-1→4 glucanase or said β-glucosidase.

10. The method as described in claim 9 wherein said pretreatment is selected from the group consisting of treatment with acid, treatment with alkali, ammonia fiber explosion, treatment with an organic solvent, autohydrolysis by steam explosion, acid steam treatment, treatment with hot, compressed liquid water, pressure cooking, milling, grinding, shearing, and extruding.

11. The method as described in claim 8 wherein said lignocellulosic material is selected from the group consisting of agricultural residues, wood, municipal solid wastes, paper and pulp industry wastes, and herbaceous crops.

12. The method as described in claim 4 further comprising fermenting said glucose to ethanol.

13. The method as described in claim 12 wherein the conversion of said cellulosic material to glucose and the fermentation of glucose to ethanol are conducted simultaneously.

14. The method as described in claim 12 wherein the conversion of said cellulosic material to glucose and the fermentation of glucose to ethanol are conducted sequentially.

* * * * *